United States Patent
Jongen et al.

(10) Patent No.: US 8,496,944 B2
(45) Date of Patent: Jul. 30, 2013

(54) PROCESS FOR THE MANUFACTURE OF POWDERS OF INHALABLE MEDICAMENTS

(75) Inventors: Nathalie Jongen, Préverenges (CH); Jacques Lemaître, Lausanne (CH); Paul Bowen, Nyon (CH); Marcel Donnet, Cheseaux (CH); Joerg Schiewe, Mainz (DE); Bernd Zierenberg, Bingen (DE); Cristina Lucica Soare, Lausanne (CH)

(73) Assignees: Boehringer Ingelheim Pharma Gmbh Co. KG, Lausanne (CH); Ingelheim am Rhein, Lausanne (CH); Germany and Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 12/263,818

(22) Filed: Nov. 3, 2008

(65) Prior Publication Data

US 2009/0068275 A1    Mar. 12, 2009

Related U.S. Application Data

(62) Division of application No. 10/685,254, filed on Oct. 14, 2003, now abandoned.

(60) Provisional application No. 60/425,415, filed on Nov. 12, 2002.

(30) Foreign Application Priority Data

Oct. 17, 2002   (EP) ..................................... 02023273

(51) Int. Cl.
*A61K 9/14*   (2006.01)
(52) U.S. Cl.
USPC .......................... 424/400; 424/489
(58) Field of Classification Search
None
See application file for complete search history.

(56) References Cited

U.S. PATENT DOCUMENTS

| | | | |
|---|---|---|---|
| 6,458,335 B1 * | 10/2002 | Lemaitre et al. | 423/419.1 |
| 2003/0180283 A1 * | 9/2003 | Batycky et al. | 424/130.1 |

FOREIGN PATENT DOCUMENTS

| | | | |
|---|---|---|---|
| DE | 1262240 | | 3/1999 |
| WO | 9802237 | A | 1/1998 |
| WO | WO0038811 | A | 7/2000 |
| WO | 0200200 | A | 1/2002 |
| WO | 02089942 | A | 11/2002 |
| WO | WO 02089942 | * | 11/2002 |

OTHER PUBLICATIONS

Linda J McCausland and Peter W Cains dds&s vol. 2 No. 2 Jun./Jul. 2002, p. 47-51.*
"Sonocrystallization—ultrsonically promoted crystallization for the optimal isolation of drug actives" by: Linda J. McCausland and Peter W. Cains., The Brititsh Librabry "The Worlds Knowledge" vol. 2 No. 2, pp. 47-51 Jun./Jul. 2002.
International Search Report for International Application PCT/EP03/11010.

* cited by examiner

*Primary Examiner* — Brian Gulledge
*Assistant Examiner* — Snigdha Maewall
(74) *Attorney, Agent, or Firm* — Michael P. Morris; David L. Kershner

(57) ABSTRACT

The invention relates to an improved process for the production of powders of an inhalable medicament by crystallization from a supersaturated fluid containing said medicament, the method comprising passing along a tubular reactor
 (a) a segmented flow of that fluid comprised of discrete volumes; or
 (b) a fluid mixture being separated by discrete volumes of a separating fluid which is substantially immiscible with said fluid,
characterized in that the crystallization is initiated by application of ultrasound.

8 Claims, 3 Drawing Sheets
PROCESS FOR THE MANUFACTURE OF POWDERS OF INHALABLE MEDICAMENTS

CROSS REFERENCE TO RELATED APPLICATIONS

This application is a divisional application of U.S. patent application Ser. No. 10/685,254, filed Oct. 14, 2003, which claims the benefit of U.S. Provisional Patent Application No. 60/425,415, filed Nov. 12, 2002, both of which are hereby incorporated herein by reference in their entireties.

BACKGROUND OF THE INVENTION

1. Technical Field

The invention relates to an improved process for the production of powders of organic compounds by precipitation from liquid mixtures.

2. Background Information

The international patent application WO 98/2237 discloses a process for the production of inorganic powders by precipitation from a liquid reaction mixture, the method comprising passing along a tubular reactor a segmented reaction flow comprised of discrete volumes of the reaction mixture separated by discrete volumes of a separating fluid which is substantially immiscible with said reaction mixture, the residence time of said discrete volumes of reaction mixture in the reactor being sufficient for the precipitation reaction to be effected.

Unfortunately, this process is not applicable for inhalable medicaments.

For inhalable medicaments, a well-defined size and shape of the crystals is a pre-requisite. In order for a powdered compound or composition to be used in an inhaled medicament, the powder must have certain characteristics. For example, micronised medicaments or active ingredients generally come in solid form. In order to guarantee the inhalability of a powdered medicament, high requirements are placed on the particle size, the particle size distribution, the morphology, the stability and the flow performance of the powder holding the medicament.

In general, the entire administered dose of the medicament does not reach the lungs. Rather, only a part of the dose does. The particle size has a substantial influence on the proportion of the medicament which actually reaches the lungs. For this reason, particles are preferred which have a diameter of less than 20 μm, preferably less than 5 μm and greater than 0.3 μm. The diameter of the particle should be within the given window and furthermore should have the narrowest possible size distribution. Larger particles are separated off during respiration in the upper airways whilst smaller particles are not deposited in the lungs and these leave again when exhaling.

Therefore, there is a great requirement for processes which achieve powders of inhalable medicaments with uniform shape, small size and narrow size distribution.

It is known that crystallization of drug actives can be ultrasonically promoted, e.g. Causland and Cains in Drug Delivery Systems & Sciences, Volume 2 No. 2, June/July 2002, pp. 47-51.

However, there is no hint that the application of ultrasound to a tubular reactor with a segmented reaction flow would yield such a desired crystal formation.

BRIEF SUMMARY OF THE INVENTION

It has now been found surprisingly, that the application of ultrasound to a tubular reactor with a segmented reaction flow achieves crystals of inhalable medicaments with the desired shape and size.

Therefore, the invention relates to an improved process for the production of powders of inhalable medicaments by crystallization from a supersaturated fluid containing said medicament, the method comprising passing along a tubular reactor (a) a segmented flow of that fluid comprised of discrete volumes; or (b) a fluid mixture being separated by discrete volumes of a separating fluid which is substantially immiscible with said fluid, characterized in that the crystallization is initiated by application of ultrasound.

A second embodiment of the present invention is a microreactor for implementing the process according to this invention comprising a micro-mixer, a segmenter and a tubular reactor, wherein the dimensions of the micro-mixer for dividing the added fluids which are to be mixed is in the range of 10 μm to 1 mm, preferably between 25 μm to 200 μm, the dimensions of the channels of the segmenter lie in the range of 0.1 to 5 mm, preferably in the range of between 0.2 mm and 5 mm, and the tubular reactor is configured to be tube-, pipe- or channel-shaped with diameters of the channels in the range of 0.5 to 10 mm, preferably 1 mm to 2 mm, and with a length of between 10 cm and 20 μm, preferably between 1 m and 25 m and is equipped with an external ultrasound source.

Furthermore the invention relates to an inhalable medicament with an aerodynamic diameter of less than 20 μm, preferably less than 5 μm and greater than 0.3 μm, characterized in that it is produced by means of the inventive process.

Figure 1:
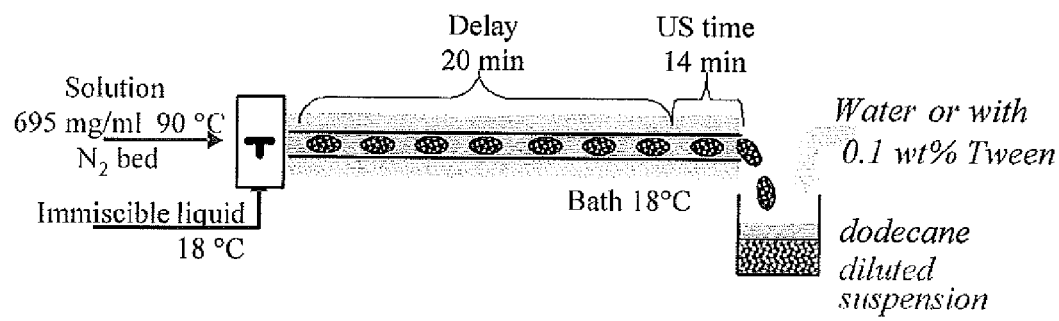
FIG. 1 shows a schematic flow chart of fenoterol crystallization.

FIG. 4 shows a schematic flow chart of Budesonide (11.07.02-SFTR) crystallization FIG. 5 shows the X-rays diffractogram of budesonide powder crystallised and reference material.

DETAILED DESCRIPTION OF THE INVENTION

The invention preferably relates to a process wherein the segmented flow passes along the tubular reactor as a plug flow.

Furthermore preferred is a process wherein the tubular reactor consists of the following segments:

(i) a residence time ($t_R$) segment;

(ii) an ultrasound time ($t_{US}$) segment, in particular wherein $t_{US}$ is 1 to 30 s or wherein $t_{US}$ is 0.5 to 15 min and $t_A$ is 0 to 30 s; and (iii) optionally an aging time ($t_A$) segment.

The particle size distribution of the organic compounds can be fine-tuned depending on the ratio of $t_R$, $t_{US}$ and $t_A$. Smaller particle size distributions can be obtained if longer $t_{US}$ are applied.

Preferably an ultrasound with a frequency of 20 to 60 kHz and/or an energy density from 10 to 80 $WL^{-1}$ is applied.

Another preferred embodiment is a process wherein the segmented flow or a precursor segmented flow from which the segmented flow is subsequently generated. is produced by passing the fluid containing the organic compound or a component thereof and the separating fluid to a chamber having a restricted outlet from which the segmented flow issues, in particular wherein the segmented flow is produced in a segmentation arrangement comprised of two concentric tubes, said chamber being provided at the outlet of the inner of the tubes and said chamber has an internal diameter of 2 mm to 10 mm.

Preferably, the innermost tube has an internal diameter of 0.1 to 2 mm and/or the distance between the outlet of the innermost tube and the inlet of the restriction is in the range 0.1 to 5 mm.

Preferably the separating fluid is passed to said chamber along the innermost tube.

Furthermore preferred is a process wherein the segmented flow is prepared by passing the fluid containing the organic compound and the separating fluid to said chamber thereby producing the segmented reaction flow, in particular wherein discrete volumes of said component of the fluid comprising the organic compound are separated by discrete volumes of the separating fluid and the segmented reaction flow is produced by admixing said discrete volumes of the fluid containing said organic compound with the remaining component(s) of the mixture.

Another preferred embodiment is a process wherein the segmented reaction flow is prepared from said precursor flow by injecting said latter flow and the further component(s) of the fluid containing the medicament to a chamber having a restricted outlet under conditions such that said further component(s) of the reaction mixture become admixed with the discrete volumes of said first component of the reaction mixture whereby the segmented reaction flow is produced, in particular wherein the segmented reaction flow is produced in a mixing arrangement, in particular wherein the chamber of the mixing arrangement has a diameter of 9 mm to 10 mm, having preferably an internal diameter of 0.1 to 2 mm, comprised of two concentric tubes said chamber being provided at the outlet of the inner of the two tubes; and/or wherein the distance between the outlet of the innermost tube of the mixing arrangement and the inlet of the restriction is in the range 0.1 to 5 mm.

Furthermore preferred is a process wherein a fluid mixture containing the medicament is prepared in a micro-mixer before the segmentation, in particular wherein the fluid mixture is a mixture of a solution of the medicament with a suitable precipitant to create a meta-stable supersaturated fluid.

Another preferred embodiment is a process wherein the fluid mixture is a mixture of a solution of the medicament with a suitable detergent in order to influence particle size and shape during the subsequent crystallization process.

Preferably the separating fluid is
a hydrocarbon, in the event that the organic compound is water-soluble, in particular a $C_{6-18}$ hydrocarbon; or
a lower alcohol or water, in the event that the organic compound is insoluble in water.

In the following text, examples are listed for the active ingredients, the adjuvants, the solvent and the precipitation agent.

The following are used as medicaments or active ingredients:
as anticholinergics: ipratropium bromide, oxitropium, tiotropium bromide, tiotroprium bromide-monohydrate,
as betasympathomimetics: bambuterol, bioiterol, carbuterol, formoterol, clenbuterol, fenoterol, hexoprenalin, procaterol, ibuterol, pirbuterol, tulobuterol, reproterol, salbutamol, salmeterol, sulfonterol, terbutalin, orciprenalin, 1-(2-fluoro-4-hydroxy-phenyl)-2-[4-(1-benzimidazolyl)-2-methyl-2-butylamino]ethanol, erythro-5'-hydroxy-8'-(1-hydroxy-2-isopropylaminobutyl)-2H-1,4-benzoxazin-3-(4H)-one, 1-(4-amino-3-chloro-5-trifluoromethyl-phenyl)-2-tert.-butylamino)ethanol, 1-(4-ethoxycarbonylamino-3-cyano-5-fluorophenyl)-2-(tert.-butylamino)ethanol, as antiallergics: disodiumchromeglicate, nedocromil, epinastin, and as steroids: flunisolide, dexamethasone-21-isonicotinate, seratrodast, mycophenolate mofetil, pranlukast, zileuton, butixocort, budesonide, deflazacort, fluticasone, proedrol, mometasin furoate, tipredan, beclometasone (or the 16,21-dipropionate), beclometasone, Douglas, icomethasone enbutate, cyclometasone, cloprednol, fluocortin butyl, halometasone, deflazacort, alclometasone, cyclometasone, alisactide, prednicarbate, hydrocortisone-butyratepropionate, tixocortolpivalate, alclometaszone-dipropionate, lotrisone, canesten-HC, deprodone, fluticasone-propionate, methylprednisolone-aceponate, halopredone-acetate, mometasone, mometasone-furoate, hydrocortisone-aceponate, mometasone, ulobetasol-propionate, aminogluethimide, triamciolone, hydrocortisone, meprednisone, fluorometholone, dexamethasone, betamethasone, medrysone fluclorolone acetonide, fluocinolone acetonide, paramethasone-acetate, deprodon propionate, aristocort-diacetate, fluocinonide, mazipredone, difluprednate, betamethasone valerate, dexamethasoneisonicotinate, beclomethasone-dipropionate, fluocortoloncapronate, formocortal, triamcinolon-hexacetonide, cloprednol, formebolone, clobetasone, endrisone, flunisolide, halcinonide, fluazacort, clobetasol, hydrocortisone-17-butyrate, diflorasone, fluocortin, amcinonide, netamethasone dipropionate, cortivazole, betamethasoneadamantoate, fluodexane, trilostan, budesonide, clobetasone, demetex, trimacinolone benetonide, 9. alpha.-chloro-6.alpha.-fluoro-11.beta. 17. alpha.-dihydroxy-16.-alpha.-methyl-3-oxo-1,4-androstadiene-17.beta.-carboxy acid methylester-17-propionate, ST-126.

Other medicaments produced with the process according to the invention are montelukast and pramipexole.

As adjuvants for inhalatives, especially lactose, glucose, sucrose, mannitol and/or trehalose are used.

Examples of solvent and precipitation agents, depending on the medicaments which are to be produced, are shown in the following tables, wherein solvents and precipitation agents must be miscible.

For anticholinergics/betasympathomimetics/antiallergics:

| Active Ingredient | Solvent | Precipitating Agents |
|---|---|---|
| Salt forms | Water, methanol | Alcohols (ethanol, propanol, iso-propanol), ketones (acetone, butanone) |
| Free bases | Alcohols (ethanol, propanol, iso-propanol, tert.-butanol), ketones (acetone, butanone) | Water, methanol |

For steroids:

| Active Ingredient | Solvent | Precipitating Agents |
|---|---|---|
| Polars | Ketones (acetone, butanone) | Alcohols (methanol, ethanol) |
| | Alcohols (ethanol, propanol, iso-propanol, tert.-butanol), ketones (acetone, butanone) | Water, methanol |
| | Aromatics (toluene, ethylbenzene) | Alcohols (ethanol, propanol, iso-propanol) |
| Unpolar | Halogen hydrocarbons (dichloromethane, trichloromethane) | Alcohols (ethanol, propanol, iso-propanol), ether (dimethylether, dioxane) |

Examples of transport media are shown in the following tables, dependent on the active ingredients which are to be produced and the solvents which are used, wherein solvents and transport media are not miscible.

| Active Ingredients | Solvents | Transport Media |
|---|---|---|
| Polar | Water, alcohols (methanol, ethanol iso-propanol, tert.-butanol), ketones (acetone,, propanol, butanone) | Fluids: hydrocarbons (benzene, petrolether, cyclohexane, decaline, dodecane, benzene, toluene, xylene) Gases: air, nitrogen, carbon dioxide, helium, argon |
| Unpolar | Halogen hydrocarbons (dichloromethane, trichloromethane), ether (diethylether, dibutylether), aromatics (toluene, ethylbenzene) | Fluids water, alcohols (methanol), amides (formamide) Gases: air, nitrogen, carbon dioxide, helium, argon |

Procedures by way of examples and drawings carrying out the process according to the invention will be described in more detail hereinafter. The Examples which follow serve solely as a detailed illustration without restricting the subject matter of the invention.

Example 1

Continuous Crystallization of Inhalable Fenoterol HBr Using a Microreactor

In order to crystallize fenoterol HBr with a particle size suitable for inhalation (90% of all crystals are smaller than 5.8 μm) a segmented flow tubular reactor was used. Fenoterol was crystallized from water by cooling, dodecane has been used as transport medium for segmentation and formation of small water bubbles.

The following parameters must be employed in order to achieve a crystal size small enough to be suitable for inhalation:
- the starting material must be a solution with a high concentration of fenoterol in water (695 mg/ml, prepared at 90° C.), which in fact represents a liquid two phase mixture
- an additive (dodecane, 6% v./v.) needs to be added to the hot solution
- from this solution a very high supersaturation is created by rapid cooling down to 18° C.
- the cooled homogeneous supersaturated solution is then allowed to rest for 22 minutes
- crystallization is induced inside small bubbles of solution by ultrasonication, the ultrasound is applied for 14 minutes
- the suspension formed is stabilized by addition of water containing a detergent (0.1 w.-% TWEEN surface active agent. TWEEN is a trademark of ICI Americas Inc. for surface active agents, and emulsifying, dispersing, solubilizing and melting agents).

Experimental:

The experiments were performed by dissolving 34.5 g fenoterol HBr in 50 ml of water. The solution was heated up to 90° C. in a thermostatic bath under nitrogen gas flow to dissolve the fenoterol. 3 ml of dodecane are added to the solution before the start of the experiment.

The solution is pumped through the reactor and enters the segmenter were small droplets are formed by segmentation with a transport fluid, dodecane at 18° C. The droplets travel for 22 minutes through the tube before being treated for to 14 minutes with ultrasound. Upon ultrasound treatment a highly concentrated suspension is formed inside the water phase which leaves the reactor together with the transport medium. The separation between the slurry and the transport medium was made in an open beaker to which pure water or an aqueous solution of 0.1 w.-% of TWEEN 80 surface active agent was added (with a (dodecane+slurry)/water ratio of about one) (see FIG. 1).

Results:

Table 1 presents the particle size distribution measured in aqueous suspension.

TABLE 1

Particle size distribution data determined in suspension measured with the Malvern Mastersizer

| Sample | $d_{v10}(\mu m)$ | $d_{v50}(\mu m)$ | $d_{v90}(\mu m)$ | Span | Medium |
|---|---|---|---|---|---|
| SFTR-14.05.02 | 1.21 | 2.51 | 5.20 | 1.59 | aqueous suspension |
| SFTR-13.06.02 | 0.77 | 1.70 | 5.92 | 3.03 | (using TWEEN surface active agent) stabilized aqueous suspension |

Figure 2:
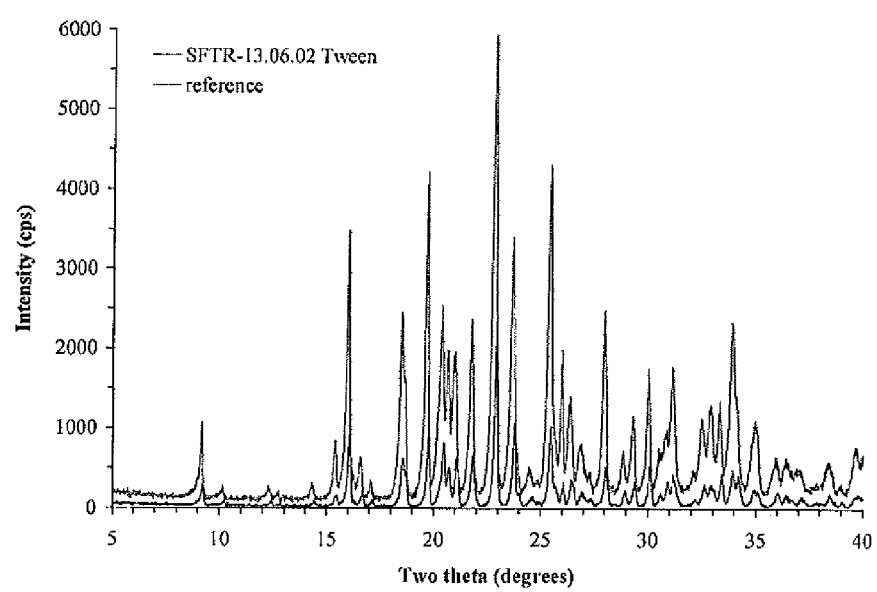
FIG. 2 shows the X-Ray diffractogram of dried sample of fenoterol (SFTR-13.06.02) TWEEN™ surface active agent and the reference powder.

The sample was also characterized by X-ray diffraction and thermoanalysis. The powder produced by filtration and drying of the suspension was fully crystalline and conform to the starting material (FIG. 2).

Figure 3:
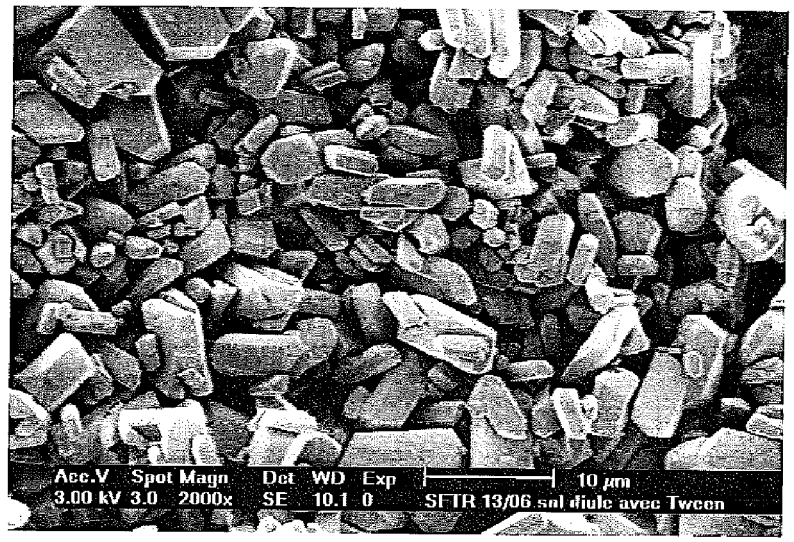
FIG. 3 shows the SEM image of dried material of fenoterol (SFTR-13.06.02) and TWEEN™ surface active agent.
Figure 4:
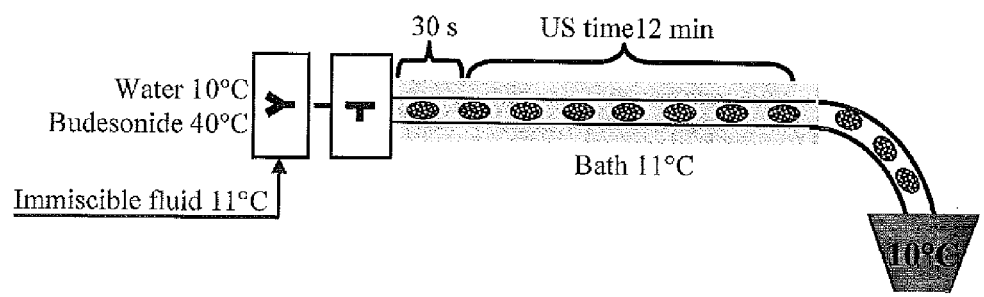
Figure 5:
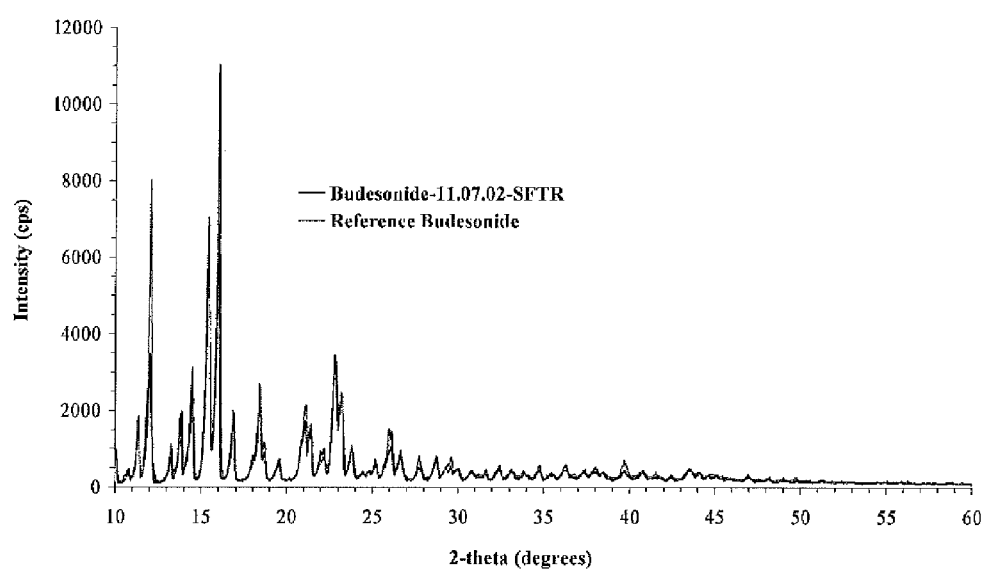

Furthermore, DSC and TGA show equivalence between starting material and crystallization product. FIG. 3 shows a SEM image of the powder.

Example 2

Continuous Crystallization of Inhalable Budesonide Using a Microreactor

Budesonide was crystallized from ethanol by a combined antisolvent and cooling crystallization using the segmented flow tubular reactor.

The following parameters must be employed in order to achieve a small crystal size:

- the starting material must be a solution with a high concentration of budesonide in ethanol (60 mg/ml, prepared at 60° C.)
- an additive (hydroxy-propyl cellulose, 1 w.-%) needs to be added to the hot solution
- from this solution a very high supersaturation is created by mixing with water (1:1) as antisolvent and simultaneous cooling down to 11° C.
- the cooled homogeneous supersaturated solution is then allowed to rest only for 30 seconds
- crystallization is induced inside small bubbles of solution by ultrasonication, the ultrasound is applied for 12 minutes Experimental:

3 g budesonide were dissolved in 50 ml of ethanol at 60° C. and allowed to cool to 40° C. 50 ml water containing 1 w.-% of hydroxy-propyl cellulose were used as antisolvent and cooled down to 10° C.

The dodecane was saturated with ethanol prior to the experiment to avoid a diffusion of the ethanol into the dodecane phase. The dodecane was injected at the temperature of 11° C. and the thermostatic bath around the tubular section of the segmented flow tubular reactor was also maintained at 11° C. The warm ethanolic solution of budesonide was mixed with cold antisolvent using a 2-jet mixer at a volume ratio ethanol/water of 1:1. The droplets were allowed to travel through the tube for 30 seconds before they undergo an ultrasonic treatment of 12 minutes where the tube is placed in an ultrasonic bath (FIG. 4). The budesonide suspension together with the transport medium were collected in a beaker maintained at 10° C. This suspension was filtered and dried over silica gel at room temperature. The powder yield is 60%.

Results:

The particle size distribution in the suspension produced has not been measured. Table 2 shows the particle size distribution of the dry powder re-dispersed in water containing 0.1 w.-% TWEEN surface active agent. The size distribution may be different compared to the crystals in suspension due to agglomeration during drying.

TABLE 2

Particles size distribution data of budesonide powder.

| Sample | $d_{v10}$ (μm) | $d_{v50}$ (μm) | $d_{v90}$ (μm) | Span |
|---|---|---|---|---|
| Budesonide | 1.32 | 7.59 | 12.86 | 1.52 |

The sample was also characterized by X-ray diffraction. The powder produced by filtration and drying of the suspension was fully crystalline and conform to the starting material (FIG. 5).

What is claimed is:

1. A process for the production of powders of inhalable medicaments by crystallization from a supersaturated fluid comprising said medicament, the process comprising:

(i) passing along a tubular reactor which includes a residence time ($t_R$) segment, an ultrasound time ($t_{US}$) segment, and optionally an aging time ($t_A$) segment a segmented flow comprising at least one discrete volume of the supersaturated fluid separated by at least one discrete volume of a separating fluid which is substantially immiscible with the supersaturated fluid; and (ii) initiating crystallization of the supersaturated fluid by application of ultrasound only in the ultrasound time segment of the tubular reactor.

2. The process as claimed in claim 1 wherein the segmented flow passes along the tubular reactor as a plug flow.

3. The process as claimed in claim 1 wherein $t_{US}$ is 1 to 30 s and $t_A$ is 0.5 to 15 min.

4. The process as claimed in claim 1 wherein $t_{US}$ is 0.5 to 15 min and $t_A$ is 0 to 30 s.

5. The process as claimed in claim 1 wherein ultrasound with a frequency of 20 to 60 kHz is applied.

6. The process as claimed in claim 5 wherein the energy density of the ultrasound applied is from 10 to 80 $WL^{-1}$.

7. The process as claimed in claim 1 wherein the supersaturated fluid further comprises a precipitant.

8. The process as claimed in claim 1 wherein the supersaturated fluid further comprises a detergent.

* * * * *